United States Patent [19]
Ellis et al.

[11] Patent Number: 5,998,143
[45] Date of Patent: Dec. 7, 1999

[54] CYCLE SEQUENCING THERMAL PROFILES

[75] Inventors: Nicole M. Ellis, San Mateo; Deborah E. Dodge, Albany, both of Calif.; Douglas H. Smith, Centerville, Del.

[73] Assignee: The Perkin-Elmer Corporation, Foster City, Calif.

[21] Appl. No.: 08/986,176

[22] Filed: Dec. 5, 1997

[51] Int. Cl.$^6$ .............................. C12Q 1/68; C12P 19/34; C07H 21/02; C07H 21/04
[52] U.S. Cl. ............................ 435/6; 435/91.2; 536/23.1; 536/24.3
[58] Field of Search ..................... 435/6, 91.2; 536/23.1, 536/24.3; 935/76, 77, 78

[56] References Cited

FOREIGN PATENT DOCUMENTS

| | | | |
|---|---|---|---|
| WO 91/19816 | 12/1991 | WIPO | C12Q 1/68 |
| WO 95/11294 | 4/1995 | WIPO | C12M 1/38 |
| WO 97/43441 | 11/1997 | WIPO | C12Q 1/98 |

OTHER PUBLICATIONS

Don et al., "'Touchdown' PCR to circumvent spurious priming during gene amplification," *Nucleic Acids Research* 19(14):4008 (Apr. 4, 1991).

D'Aquila et al., "Maximizing sensitivity and specificity of PCR by pre–amplificatin heating," *Nucleic Acids Research* 19(13):3749 (Apr. 9, 1991).

Murray, Vincent, "Improved double–stranded DNA sequencing using the linear polymerase chain reaction," *Nucleic Acid Research* 17(21):8889 (Nov. 11, 1989).

Carothers et al., "Point Mutation Analysis in a Mammalian Gene: Rapid Preparation of Total RNA, PCR Amplification of cDNA, and Tag Sequencing by Novel Method," *BioTechniques* 7(5):494–496, and 498–499 (May 1989).

Compton, Teresa, "Degenerate Primers For DNA Amplification," *PCR Protocols: A Guide to Methods and Applications* Innis et al. ed., Academic Press, San Deigo, CA Chapter 5 pp. 39–45 (1990).

Shen et al., "Cycle Sequencing Using Degenerate Primers Containing Inosines," *BioTechniques* 15(1):82, 84, and 88–89 (Jul. 1993).

Voss et al., "Automated Cycle Sequencing with Taquenase™: Protocols for Internal Labeling, Dye Primer and "Doublex" Simultaneous Sequencing," *BioTechniques* 23(2):312–318 (Aug. 1997).

Ruano et al., PNAS 88 : 2815–2819 (1991).
Weissensteiner et al., Biotechniques 21(6) : 1102–1108 (1996).
Hecker et al., Biotechniques 20(3) : 478–485 (1996).
Chiang et al., Clinical Chemistry 44(6) : (Jun. 1998).
Horton et al., PCR Methods and Applications 3 : 359–360 (1994).

*Primary Examiner*—Stephanie Zitomer
*Assistant Examiner*—Ethan Whisenant

[57] ABSTRACT

The present invention relates to improved methods of generating polynucleotide sequencing reaction products from cycle sequencing and relates to various instruments and reagents for use in the subject methods. The use of "step-down" thermal profiles in conjunction with cycle sequencing is described. Step-down thermal profiles are formed by combining several thermal cycle sets such that the annealing temperature of each thermal cycle set is less than the annealing temperature of the preceding thermal cycle set. One embodiment of the invention is a method of generating a plurality of polynucleotide sequencing reaction products in parallel by subjecting a plurality of sequencing solution preparations to a step-down thermal profile, i.e., exposure to repeated thermal cycle sets, each thermal cycle set having an annealing temperature that is lower than the annealing temperature of the annealing phases of the preceding thermal cycle set. Other embodiments of the invention include systems for generating a plurality of polynucleotide sequencing reaction products in parallel. The systems comprise (i) a programmable thermal cycler programmed to perform a step-down thermal profile and (ii) a plurality of polynucleotide sequencing preparations. Additional embodiments of the invention include sets of polynucleotide sequencing reaction preparations that may be used in the methods of the invention.

Another aspect of the invention is a device for generating a plurality of polynucleotide sequencing reaction products. The devices of the invention include (i) a plurality of polynucleotide sequencing reaction preparation chambers, each chamber containing a sequencing primer, (ii) a common fluid entry port, and (iii) a fluid dispensing channel, the channel connecting each of the sequencing reaction preparation chambers to the common fluid entry port. At least two of the sequencing primers in the device have Tms different from one another by at least 2° C.

5 Claims, 1 Drawing Sheet

CYCLE SEQUENCING THERMAL PROFILES

The determination of the base sequence of polynucleotides has become a pivotal technique in genetic analysis. Many techniques for determining polynucleotide sequences have been developed. Foremost among these techniques is Sanger sequencing involving the use of 2'3' dideoxynucleotides as chain terminators for the generation of sequencing reaction products that may be analyzed by electrophoresis. A recently developed variation on the method Sanger sequencing is cycle sequencing. Cycle sequencing is described in, among other places, Caruthers et al., *Biotechniques* 7:494–499 (1989) and Murray et al., *Nucleic Acids Res.* 17:88–89 (1989). Cycle sequencing involves the use of a thermostable DNA polymerase and repeated cycles of sequencing primer annealing, extension, and denaturation to achieve linear amplification of the sequencing reaction products. Cycle sequencing is particularly useful when the sequencing template is present in small quantities. Difficulties may arise when attempting to carry out several cycle sequencing reactions in parallel in the same thermal cycler instrument. These difficulties result from differences between the Tm of different sequencing primers. Primers having different Tins require thermal cycling procedures having different parameters in order to generate large quantities of useful sequence information. This requirement for different thermal cycle parameters for different primers necessitates performing the cycle sequencing reactions with primers having significantly different Tms in successive runs of thermal cycler instruments (or the use of multiple instruments). Another problem with the use of cycle sequencing is the generation of sequencing artifacts, e.g. resulting from non-specific priming, caused by the use of suboptimal thermal cycle parameters.

In view of the above problems with cycle sequencing, it is of interest to provide improved methods and systems for performing multiple cycle sequencing reactions in parallel. It is also of interest to develop new techniques for reducing the number of artifacts associated with cycle sequencing.

SUMMARY

The present invention relates to improved methods of generating polynucleotide sequencing reaction products from cycle sequencing and relates to various instruments and reagents for use in the subject methods. The use of "step-down" thermal profiles in conjunction with cycle sequencing is described. Step-down thermal profiles are formed by combining several thermal cycle sets such that the annealing temperature of each thermal cycle set is less than the annealing temperature of the preceding thermal cycle set. The invention may be used to generate in parallel a plurality of polynucleotide sequencing reaction products produced from sequencing primers that have different Tms. The invention may also be used to obtain superior sequence information from single polynucleotide sequencing reaction products.

One embodiment of the invention is a method of generating a plurality of polynucleotide sequencing reaction products in parallel by subjecting a plurality of sequencing solution preparations to a step-down thermal profile, i.e., exposure to repeated thermal cycle sets, each thermal cycle set having an annealing temperature that is lower than the annealing temperature of the annealing phases of the preceding thermal cycle set. The thermal cycles in a thermal set may optionally have a separate extension phase at temperatures different than the annealing temperature. The extension temperature of the extension phase of subsequent thermal cycle sets may also be lower than the extension temperature of the extension phase of preceding thermal cycle sets.

Other embodiments of the invention include systems for generating a plurality of polynucleotide sequencing reaction products in parallel. The systems comprise (i) a programmable thermal cycler programmed to perform a step-down thermal profile and (ii) a plurality of polynucleotide sequencing preparations. an extension phase (for the extension of the annealed primers) that takes place at a temperature said to be the extension temperature, and a denaturation phase (for denaturing the extended primer and the template) that takes place at a temperature said to be the denaturation temperature. The annealing phase and the extension phase may be combined into a single phase taking place at a single temperature; this combined annealing phase and extension phase is referred to collectively as an annealing phase. Each phase takes place for a specified period of time. Thus, a given thermal cycle may be characterized by three temperature parameters and three time parameters, or in embodiments of the invention having a combined annealing and extension phase, a given thermal cycle may be characterized by two temperature parameters and two time parameters.

A thermal cycle set is defined herein to be one or more sequentially performed thermal cycles with the same annealing temperature and extension temperature parameters. All the temperature parameters of the thermal cycles that constitute a thermal cycle set are identical to one another. Preferably, all the time and all the temperature parameters of the given thermal cycles that constitute a thermal cycle set are identical to one another. A thermal cycle may consist of a single thermal cycle, such thermal cycle sets are referred to as unitary thermal cycle sets.

The term "sequencing reaction preparation" refers to a mixture, typically in solution, of the reagents that is sufficient to produce polynucleotide sequencing reaction products from a cycle sequencing reaction. Exemplary of sequencing reaction preparation is: a sequencing reaction preparation contains a sequencing primer, a suitable reaction buffer, a thermostable DNA polymerase, 2'3'dideoxynucleotides (or functional equivalents thereof), and deoxynucleotides. The dideoxynucleotides of the primers may be flourescently labeled so as to provided fi)r the analysis of the sequencing reaction products in an a fluorescence based polynucleotide sequence analysis system, see for example U.S. Pat. Nos. 5,543,026, 5,483,075, 5,434,049, 5,307,148, and 5,268,080. Sequencing reaction preparations may or may not contain a template for sequencing. Of course, a template for sequencing is essential if sequencing reaction products are to be produced.

The term "Tm" refers to the denaturation temperature of a given oligonucleotide when hybridized to a perfectly complementary oligonucleotide in a given environment, e.g., the buffer used for cycle sequencing. Tm may be calculated empirically. As a matter of convenience, Tm for a Other embodiments of the invention include sets of polynucleotide sequencing reaction reparations that may be used in the methods of the invention. Each of the polynucleotide sequencing reaction preparations that form the sets have a sequencing primer. At least two of the different sequencing primers in the set have Tms that differ from one another by at least 2° C.

Another aspect of the invention is a device for generating a plurality )f polynucleotide sequencing reaction products. The devices of the invention include (i) a plurality of polynucleotide sequencing reaction preparation chambers, each chamber containing a sequencing primer, (ii) a common fluid entry port, and (iii) a fluid dispensing channel, the channel connecting each of the sequencing reaction preparation chambers to the common fluid entry port. At least two of the sequencing primers in the device have Tms different from one another by at least 2° C.

DEFINITIONS

Figure 1:
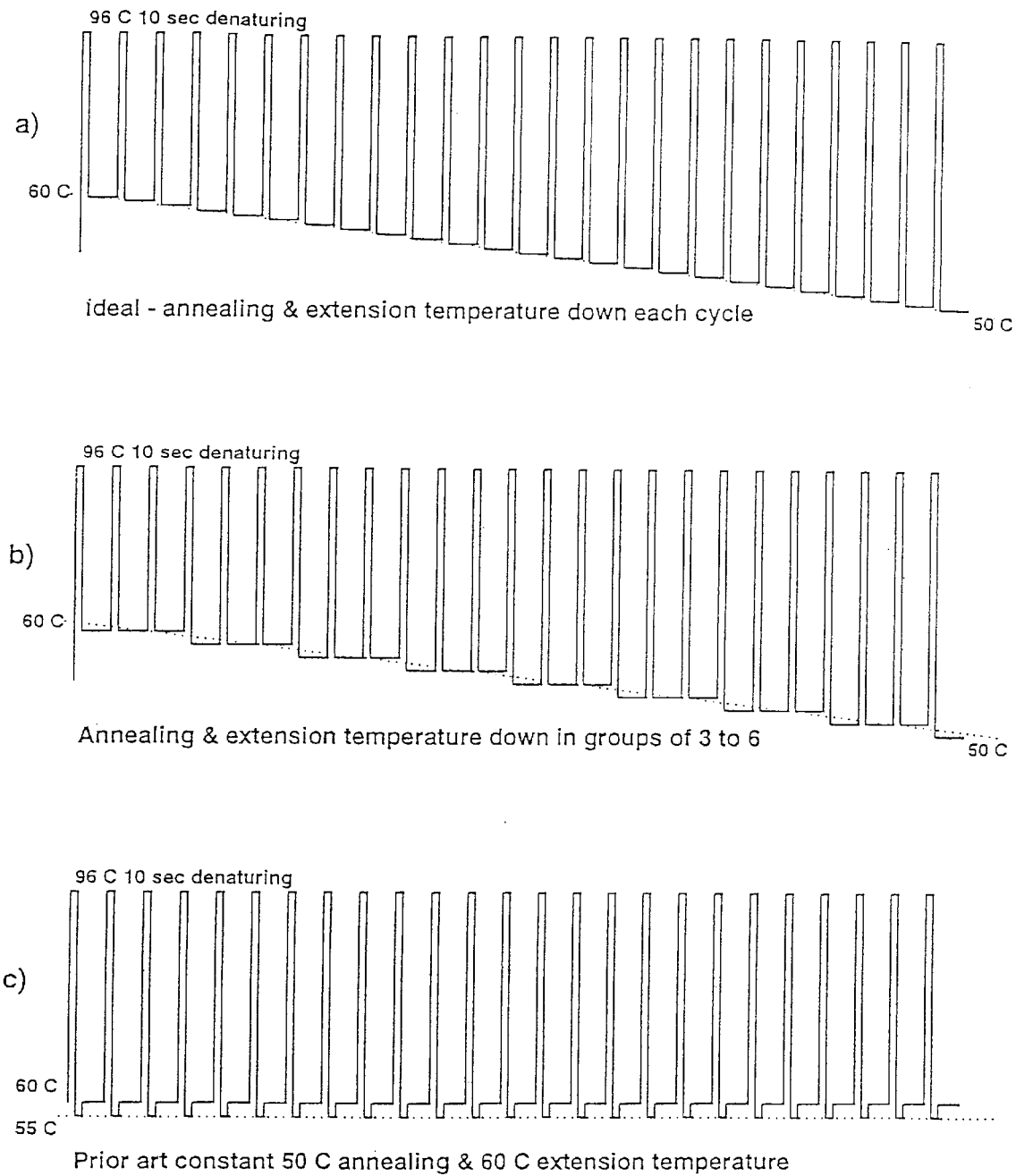
FIG. 1 provides schematic profiles of three different touch down thermal profiles. The X axis denotes time and the Y axis denotes temperature.

A description of "cycle sequencing" can be found, among other places, in Murray V., *Nucl. Acid. Res.*, 17:8889 (1989). Typically, cycle-sequencing is a polynucleotide sequencing generating technique comprising the following steps: (a) the hybridization of a primer oligonucleotide to a template for sequencing so as to form a primed template, (b) extending the primer with a DNA polymerase, (c) ending the extension reaction with a chain terminator (e.g., a dideoxy terminator), (d) denaturing the primed template, (e) repeating steps (a) to (d) for multiple cycles.

The term "thermal profile" refers to the sum of all the thermal cycles performed to produce polynucleotide sequencing reaction products from a cycle sequencing reaction. For example, a graphical representation of a thermal profile is given in FIG. 1.

A "thermal cycle," as defined herein, is a process of changing temperature in a defined volume, the process being characterized by three phases, an annealing phase (for the annealing of the primers to the template) that takes place at a temperature said to be the annealing temperature, given oligonucleotide primer may be predicted. When the oligonucleotide primer is other than DNA, the Tm calculation may take into account the differences in binding properties of the different nucleotides. In those embodiments of the invention in which a Tm can not reasonably be predicted, Tm may be calculated empirically using techniques well known to persons of ordinary skill in the art, e.g., UV absorption shift measurement upon denaturation.

The term "sequencing reaction products" as used herein refer to the labeled polynucleotides produced after performing a Sanger-type sequencing reaction with chain extension terminating nucleotide analogs. Characterization of the sequencing reaction products, e.g. by electrophoresis, is used to acertain the actual nucleotide sequence.

DESCRIPTION OF SPECIFIC EMBODIMENTS

Various embodiments of the invention relate to methods of generating polynucleotide sequencing information through cycle sequencing by using certain thermal profiles for the cycle sequencing reactions. The thermal profiles incorporated into embodiments of the invention, either directly or indirectly, employ a plurality of successively performed thermal cycles, each thermal cycle having an annealing temperature that is lower than the annealing temperature of the preceding thermal cycle. Such thermal profiles are referred to herein as "step-down" thermal profiles.

Certain embodiments of the invention may be used to perform a plurality of polynucleotide sequencing reactions in parallel. Other embodiments of the invention may be used to perform individual cycle sequencing reactions. Embodiments of the invention include methods of generating polynucleotide sequencing reaction products, systems for generating a plurality of polynucleotide sequencing reaction products in parallel, sets of polynucleotide sequencing reaction preparations for use with the subject methods, and devices for generating a plurality of polynucleotide sequencing reaction products in parallel.

Embodiments of the invention relate to the use of a specific type of thermal profile referred to herein as a "step-down" thermal profile. Each step-down thermal profile comprises at least two thermal cycle sets. Typically, a step-down thermal profile comprises 10–40 thermal cycle sets. Each thermal cycle set (other than the first thermal cycle set) of a step-down thermal profile consists of thermal cycles having a annealing temperature that is lower than the annealing temperature of the thermal cycles of the preceding thermal cycle set. In those embodiments of the invention employing thermal cycles having a separate annealing and extension phase, each thermal cycle set (other than the first thermal cycle set) of a step-down thermal profile preferably consists of thermal cycles having an extension temperature that is lower than the extension temperature of the thermal cycles of the preceding thermal cycle set. In embodiments of the invention employing step-down thermal profiles that have decreasing annealing temperature and decreasing extension temperatures in subsequent thermal cycle sets, the increments of temperature decrease between the annealing temperatures of successive thermal cycle sets is preferably the same as the increments of temperature decrease between the extension temperatures of successive thermal cycle sets.

The invention includes many different temperature increments between the annealing temperature or extension temperatures of successive thermal cycles in a step-down thermal profile. Generally, the increments are in the ranges of 0.1° C. to 3.0° C. Preferably, the temperature increments are in the range of 0.5° C. to 1.5° C., the temperature increment of 1.0° C. being particularly preferred.

The temperature increments between the annealing temperatures or extension temperatures of the successive thermal cycle sets of a given step-down thermal profile may be the same or different from one another. In a preferred embodiment, the temperature increments between the annealing temperatures (and also extension temperatures, if a separate extension temperature phase is used in that embodiment) of the successive thermal cycle sets of a given step-down thermal profile are identical to one another. The annealing temperature of the thermal cycles of the first thermal cycle is the same or higher,commonly 1° C. to 15° C. higher, than the predicted Tm of the sequencing primer having the highest Tm in the set of sequencing preparations that are to be processed in parallel. The difference between the highest and lowest annealing temperatures in a thermal profile will vary in accordance with the Tms of the specific primers in the set of sequencing preparations that are to be processed in parallel in order to provide for sequence product generation from all the template-primer combinations.

The number of thermal cycles in each thermal cycle set of a step-down thermal profile may be the same or different than one another. In a preferred embodiment of the invention, the number of thermal cycles in each thermal cycle set of a step-down thermal profile is the same. The number of thermal cycles in a thermal cycle set of a step-down thermal profile is variable. Typically, although not necessarily, the number of thermal cycles in a thermal cycle set of a step-down thermal profile is in the range of 1 to 10 (and ranges inclusive thereof) such as 1 to 5 and 1 to 3. Step-down thermal profiles may consist of a series of unitary thermal cycle sets.

One embodiment of the invention is to generate polynucleotide sequencing reaction products using a step-down thermal profile. The method comprises exposing a polynucleotide sequencing preparation to a step-down thermal profile. The use of a step-down thermal profile for cycle sequencing avoids problems stemming from improper annealing between a sequencing primer and its cognate template. Thus, a higher amount of correctly annealed (i.e., annealed at the desired site and in the desired manner) primer-template complexes are formed, thereby resulting in improved information obtained from the sequencing products. Given that a step-down thermal profile results in primer-template annealing that may take place below optimal temperatures, the superior sequencing results obtained with the various embodiments are unexpected.

Another aspect of the invention is to provide methods of generating a plurality of polynucleotide sequencing reaction products in parallel. The methods comprise the steps of exposing at least two polynucleotide sequencing preparations to a step-down thermal profile. The use of a step-down thermal profile to generate a plurality of polynucleotide sequencing reaction products in parallel is advantageous because, among other reasons, sequencing primers with significantly different Tms may be used in parallel in the same thermal cycling instrument.

Additional embodiments of the invention include systems for generating a plurality of polynucleotide sequencing reaction products in parallel. These systems comprise (i) a programmable thermal cycler programmed to execute a step-down thermal profile on samples placed in the sample heating chamber(s) at the thermal cycler, and (ii) a plurality of polynucleotide sequencing reaction preparations in functional contact with the sample heating chamber. The term "functional contact" is used to indicate that the heating chamber contacts the sample(usually present in sealed vessel) in such a way as to modify the temperature of the sample in accordance with the temperature of the heating block. Thus the temperature of the sample rises or falls in conjunction with rises and falls of the temperature of the heating chamber (or equivalent robotic multiblock systems such as those described in U.S. Pat. No. 5,525,300).

A wide variety of thermal cyclers may be used in the systems of the invention or to perform the methods of the invention. Programmable thermal cyclers, capable of being programmed to execute a step-down thermal cycle may be employed to execute a step-down thermal cycle). Thermal cyclers suitable for practicing PCR (polymerase chain reaction) are generally suitable for use in the systems of the invention and for performing the methods of the invention. Such thermal cyclers and their use are described in, among other places, in U.S. Pat. Nos. 5,601,141; 5,525,300; 5,602, 756; 5,616,301; 5,187,084; and 5,435,378. Numerous commercially-available thermal cycler instruments may be used such as the Perkin-Elmer 9600 (Norwalk, Conn., U.S.A.).

The thermal cyclers for use in the subject systems comprise a sample heating chamber (or chambers) for exposing samples, i.e., vessels containing polynucleotide sequencing reaction preparations, to thermal cycles.

Other embodiments of the invention include sets of polynucleotide sequencing reaction preparations that may be processed in parallel by exposure to a step-down thermal profile so as to produce the desired polynucleotide sequencing reaction products. The subject sets of polynucleotide sequencing reaction preparations comprise at least two sequencing primers having Tms that differ by at least 2° C. The subject sets of polynulceotide sequencing reaction preparations may comprise at least two sequencing primers that have Tms that differs by more than 2° C., e.g., 3–10° C. (inclusive), and the like. Absent the use of step-down thermal profiles for generating a plurality of polynucleotide sequencing reaction products in parallel, there would be no reason to produce the subject sets of polynucleotide sequencing reactions because of the failure of the different primers to properly anneal when subjected to a conventional thermal profile.

Typically, the primers included in the subject sets of polynucleotide sequencing reaction preparations are supplied in separate solutions; each polynucleotide sequencing reaction preparation having a single primer. However, the sets of polynucleotide primers may be supplied in the same solution so as to facilitate various forms of multiplex DNA sequencing. Optionally, the subject primer sets may be designed so as to generate polynucleotide sequencing reaction products (and hence sequence information) from regions of a template spaced sufficiently close together to produce contiguous or substantially contiguous sequence information. Such as embodiments of the sets of polynucleotide primers are particularly useful for generating the complete sequence of a gene or a significant portion thereof.

Other embodiments of the invention include devices for generating a plurality of polynucleotide sequencing reaction products in parallel. The subject devices generate the polynucleotide sequencing reaction products in parallel. The subject devices generate different sets of polynucleotide sequencing reaction products from a common DNA (or other polynucleotide) containing sample introduced in the device. The sample contains the DNA templates for annealing to the different sequencing primers present in the device. The subject devices comprise a plurality of polynucleotide sequencing reaction chambers, a fluid entry port, and a fluid dispensing channel. The fluid dispensing channels connect each of the sequencing reaction chambers to a fluid entry port. The polynucleotide sequencing reaction chambers are connected to the fluid entry port by the fluid dispensing channel in such a manner that a fluid sample introduced into the fluid entry port is distributed to the sequencing reaction chamber without permitting cross-contamination between the contents of the sequencing reaction chambers. The sequencing reaction chamber comprises a sequencing primer. At least two of the different sequencing primers in a given embodiment of the device have Tms differing by at least 2° C. The subject devices may be used by introducing a sequencing template containing solution into the fluid entry port and allowing the template containing solution to be distributed to the sequencing reaction chambers. Alter the template containing solution has been distributed to sequencing reaction preparation chambers, the device is subjected to step-down thermal profile of the invention, whereby sequencing reaction products are produced. The sequencing reaction products may then be removed form the device and analyzed, e.g. by electrophoresis, so as to provide sequence information. The template containing solution introduced into the subject devices in addition to containing template, may contain one or more reagents necessary for cycle sequencing and common to all of the sequencing reactions. Such reagents include a thermostable DNA polymerase, buffer, nucleotides, dideoxynucleotides (labeled or otherwise), and the like. Alternatively, one or more of such reagents necessary for cycle sequencing may be present in the sequencing reaction chambers (prior to the addition of the template containing solution) rather than be present in the chamber.

EXAMPLES

Experiments were performed in which cycle sequencing was performed to sequence the 16S ribosomal RNA gene of *Lactobacillus casei*.

Comparisons were made between sequence information obtained under conventional thermal profile conditions and using step-down thermal profiles. The four primers tested were 0005F (annealing at position 5 of 16S gene, forward direction), 0515F (annealing at position 515 in the forward direction), 0810R (annealing at position 810 in the reverse direction), and 1540R (annealing at position 1540 in the reverse direction).

Cycle sequencing was performed using conventional cycle sequencing reagents. The following step-down thermal profile was used:

| Cycle set. # | Cycle Denature | Anneal | Hold | Number of Cycles |
|---|---|---|---|---|
| 1. | 96° C. 10 sec. | 65° C. 1 min. | — | 6 |
| 2. | 96° C. 10 sec. | 64° C. 1 min. | — | 6 |
| 3. | 96 ° C. 10 sec. | 63 ° C. 1 min. | — | 6 |
| 4. | 96 ° C. 10 sec. | 62 ° C. 1 min. | — | 6 |
| 5. | 96 ° C. 10 sec. | 61 ° C. 1 min. | — | 6 |
| 6. | 96° C. 10 sec. | 60° C. 1 min. | — | 6 |
| 7. | 96° C. 10 sec. | 59° C. 1 min. | — | 6 |
| 8. | 96° C. 10 sec. | 58° C. 1 min | — | 6 |
| 9. | 96° C. 10 sec. | 57° C. 1 min. | — | 6 |
| 10. | 96° C. 10 sec. | 56° C. 1 min. | — | 6 |
| 11. | 96° C. 10 sec. | 55° C. 1 min. | — | 6 |
|  | — | — | 4° C. forever | — |

The reactions were performed in a Perkin-Elmer Gene-Amp® System 9600 thermal cycler. The results obtained are as follows:

0005F 16S Primer
   a) Step-down thermal profile. Note improved G signal level throughout run.
   b) Conventional thermal profile. Performance is poorer.

0515F 16S Primer
   a) Step-down thermal profile. Note improved C noise under T peaks throughout run.
   b) Conventional thermal profile. Performance is poorer.

0810R 16S Primer
   a) Step-down thermal profile. Note reduced G noise throughout run.
   b) Conventional thermal profile. High G noise.

1540R 16S Primer
   a) Step-down thermal profile. Note reduced G noise throughout run.
   b) Conventional thermal profile. High G noise.

Incorporation by Reference

All papers and documents (including patents) referenced in this specification are incorporated herein by reference.

EQUIVALENTS

While the invention has been described with reference to specific methods and embodiments, it will be appreciated that various modifications and changes may be made without departing from the invention. These and other equivalents are intended to be covered by the following claims.

What is claimed is:

1. A method of generating polynucleotide sequencing reaction products, comprising the steps of
exposing a plurality of polynucleotide sequencing preparations to at least two thermal cycle sets, wherein each thermal cycle set consists of at least one thermal cycle and wherein each thermal cycle comprises an annealing phase at an annealing temperature,
and wherein each thermal cycle set other than the first thermal cycle set consists of thermal cycles having an annealing phase at an annealing temperature that is lower than the annealing temperature of the annealing phases of the preceding thermal cycle set, the thermal cycling sets being performed in the instrument, and
producing polynucleotide sequencing reaction products.

2. A method according to claim 1, wherein each thermal cycle set comprises the same number of thermal cycles.

3. A method according to claim 1, wherein the difference in annealing temperature between each thermal cycle set and the preceding thermal cycle set is the same.

4. A method according to claim 1, wherein each thermal cycle set consists of at least three thermal cycles.

5. A method according to claim 1, wherein the sequencing reaction preparations comprise a sequencing template that has been prepared by nucleic acid amplification.

* * * * *

UNITED STATES PATENT AND TRADEMARK OFFICE
CERTIFICATE OF CORRECTION

Page 1 of 2

PATENT NO. : 5,998,143
DATED : December 7, 1999
INVENTOR(S) : Nicole M. Ellis, Deborah E. Dodge, Douglas H. Smith It is certified that error appears in the above-identified patent and that said Letters Patent is hereby corrected as shown below:

Column 2, line 8, after "sequencing preparations." insert:

Other embodiments of the invention include sets of polynucleotide sequencing reaction reparations that may be used in the methods of the invention. Each of the polynucleotide sequencing reaction preparations that form the sets have a sequencing primer. At least two of the different sequencing primers in the set have Tms that differ from one another by at least 2° C.

Another aspect of the invention is a device for generating a plurality )f polynucleotide sequencing reaction products. The devices of the invention include (i) a plurality of polynucleotide sequencing reaction preparation chambers, each chamber containing a sequencing primer, (ii) a common fluid entry port, and (iii) a fluid dispensing channel, the channel connecting each of the sequencing reaction preparation chambers to the common fluid entry port. At least two of the sequencing primers in the device have Tms different from one another by at least 2° C.

BRIEF DESCRIPTION OF THE DRAWING

FIG. 1 provides schematic profiles of three different touch down thermal profiles. The X axis denotes time and the Y axis denotes temperature.

DEFINITIONS

A description of "cycle sequencing" can be found, among other places, in Murray V., Nucl. Acid. Res., 17:8889 (1989). Typically, cycle-sequencing is a polynucleotide sequencing generating technique comprising the following steps: (a) the hybridization of a primer oligonucleotide to a template for sequencing so as to form a primed template, (b) extending the primer with a DNA polymerase, (c) ending the extension reaction with a chain terminator (e.g., a dideoxy terminator), (d) denaturing the primed template, (e) repeating steps (a) to (d) for multiple cycles.

The term "thermal profile" refers to the sum of all the thermal cycles performed to produce polynucleotide sequencing reaction products from a cycle sequencing reaction. For example, a graphical representation of a thermal profile is given in FIG. 1.

A "thermal cycle," as defined herein, is a process of changing temperature in a defined volume, the process being characterized by three phases, an annealing phase (for the annealing of the primers to the template) that takes place at a temperature said to be the annealing temperature,

UNITED STATES PATENT AND TRADEMARK OFFICE
CERTIFICATE OF CORRECTION

PATENT NO. : 5,998,143

DATED : December 7, 1999

INVENTOR(S) : Nicole M. Ellis, Deborah E. Dodge, Douglas H. Smith

It is certified that error appears in the above-identified patent and that said Letters Patent is hereby corrected as shown below:

Column 2, line 42, change "provided fi)r" to - -provide for- -.

Column 2, delete lines 56 through 66.

Column 2, line 57, "reparations" should read - -preparations- -.

Column 2, line 64, "a plurality )f" should read --a plurality of- -.

Column 3, delete lines 1 through 34.

Column 3, line 35 delete "a temperature said to be the annealing temperature".

Column 4, line 34, "0.1° C." should read - -0.1° C- -.

Column 4, line 35, "0.5° C. to 1.5° C.," should read --0.5° C to 1.5° C,--.

Column 4, line 36, "1.0° C." should read - -1.0° C- -.

Column 4, line 47, "1° C." should read - -1° C- -.

Column 4, line 48, "C. higher," should read - -C higher,- -.

Column 6, line 2, "2° C., e.g., 3-10° C." to read - -2° C, e.g., 3-10° C- -.

Column 8, line 35, "in the instrument," should read - -in the same instrument,- -.

Signed and Sealed this

Fifth Day of September, 2000

Attest:

Q. TODD DICKINSON

*Attesting Officer*    *Director of Patents and Trademarks*